United States Patent
Langlade Demoyen et al.

(10) Patent No.: US 10,010,591 B2
(45) Date of Patent: Jul. 3, 2018

(54) METHOD OF TREATING FIBROSARCOMA USING A NUCLEIC ACID SEQUENCE ENCODING APOBEC3A

(71) Applicant: INVECTYS, Paris (FR)

(72) Inventors: Pierre Langlade Demoyen, Neuilly-sur-Seine (FR); Anna Kostrzak, Paris (FR); Simon Wain-Hobson, Montigny-le-Bretonneux (FR)

(73) Assignee: INVECTYS, Paris (FR)

( * ) Notice: Subject to any disclaimer, the term of this patent is extended or adjusted under 35 U.S.C. 154(b) by 0 days.

(21) Appl. No.: 14/895,532

(22) PCT Filed: Jun. 3, 2014

(86) PCT No.: PCT/EP2014/061516
§ 371 (c)(1),
(2) Date: Dec. 3, 2015

(87) PCT Pub. No.: WO2014/195331
PCT Pub. Date: Dec. 11, 2014

(65) Prior Publication Data
US 2016/0120962 A1    May 5, 2016

(30) Foreign Application Priority Data
Jun. 3, 2013 (EP) .................. 13305732

(51) Int. Cl.
| | | |
|---|---|---|
| *A01N 43/04* | (2006.01) | |
| *A61K 31/715* | (2006.01) | |
| *A01N 63/00* | (2006.01) | |
| *A01N 65/00* | (2009.01) | |
| *A61K 38/50* | (2006.01) | |
| *C12N 9/78* | (2006.01) | |
| *A61K 9/00* | (2006.01) | |
| *A61K 45/06* | (2006.01) | |
| *A61K 48/00* | (2006.01) | |

(52) U.S. Cl.
CPC ............ *A61K 38/50* (2013.01); *A61K 9/0019* (2013.01); *A61K 45/06* (2013.01); *C12N 9/78* (2013.01); *C12Y 305/04014* (2013.01); *A61K 48/00* (2013.01); *A61K 48/005* (2013.01); *C12Y 305/04* (2013.01)

(58) Field of Classification Search
USPC ................. 514/44; 424/93.2, 93.1, 93.21
See application file for complete search history.

(56) References Cited

U.S. PATENT DOCUMENTS

2009/0202488 A1* 8/2009 Lochelt ............... A61K 38/162
514/1.1

FOREIGN PATENT DOCUMENTS

| CA | 2492768 | * | 7/2006 |
| CA | 2492768 A1 | | 7/2006 |
| WO | 2008/156629 A2 | | 12/2008 |
| WO | WO 2008/156629 | * | 12/2008 |
| WO | 2010/039223 A2 | | 4/2010 |
| WO | WO 2010/039223 | * | 4/2010 |
| WO | 2011/075627 A1 | | 6/2011 |
| WO | WO 2011/075627 | * | 6/2011 |

OTHER PUBLICATIONS

Russell (J. Virol., Jul. 2005, vol. 79, No. 14, p. 8724-8731).*
Landry (EMBO Reports, 2011, vol. 12, No. 5, p. 440-450).*
Radkevich-Brown (Cancer Immunology Immunotherapy, 2010, vol. 59, p. 409-417.*
Prud'homme (Current Gene therapy, 2006, vol. 6, p. 243-273).*
Ugen (Cancer Gene Therapy, 2006, vol. 13, No. 10, p. 969-974).*
Tamura (Current Gene Therapy, 2003, vol. 3, p. 59-64).*
Gehl (Methods in Mol. Biol., 2008, vol. 423, p. 351-359).*
Gehl (Acta Physiol Scand 2003, vol. 177, p. 437-447).*
Li (Methods in Mol. Biol, 2008, vol. 423, p. 311-318).*
Yuan (BED (American Soc. of Mechanical Engineers), 2000, vol. 48, Advances in Bioengineering, p. 173-176).*
Cemazar (Current Drug Delivery, 2006, vol. 3, p. 77-81).*
Paulin (Cancer Biol. & Therapy, Nov. 2009, vol. 8, No. 22, p. 2112-2120).*
Li (Mol. Therapy, Mar. 2004, vol. 9, No. 3, p. 347-354).*
Sebastien Landry, et al.: "APOBEC3A can activate the DNA damage response and cause cell-cycle arrest", EMBO Reports, vol. 12. No. 5. May 1, 2011 (May 1, 2011), pp. 444-450.
International Search Report and Written Opinion of the ISA dated Jul. 23, 2014 issued in corresponding PCT Application No. PCT/EP2014/061516.
Exhibit B—Sequence Alignment dated Mar. 7, 2017 that was Submitted with the Response to Final Office Action dated Nov. 10, 2017, 1 pages.
International Preliminary Report on Patentability Issued in PCT/EP2014/061516, dated Dec. 8, 2015, 7 pages.
Lackey, L. et al., "Subcellular localization of the APOBEC3 proteins during mitosis and implications for genomic DNA deamination", Cell Cycle (2013), vol. 12, No. 5, pp. 762-772.
Nebel, C. et al., "AID/APOBEC deaminases disfavor modified cytosines implicated in DNA demethylation", Nature Chemical Biology (2012), vol. 8, pp. 751-758.
Teperek-Tkacz, Marta et al., "Epigenetic reprogramming—is deamination key to active DNA demethylation?", Europe PMC Funders Group (2011), vol. 142(5), 19 pages.

* cited by examiner

*Primary Examiner* — Michael C Wilson
(74) *Attorney, Agent, or Firm* — Troutman Sanders LLP

(57) ABSTRACT

The present invention relates to the use of a nucleic acid that comprises a sequence encoding an APOBEC3A protein, in preventing or treating a tumor in a patient.

6 Claims, 9 Drawing Sheets

Figure 1:
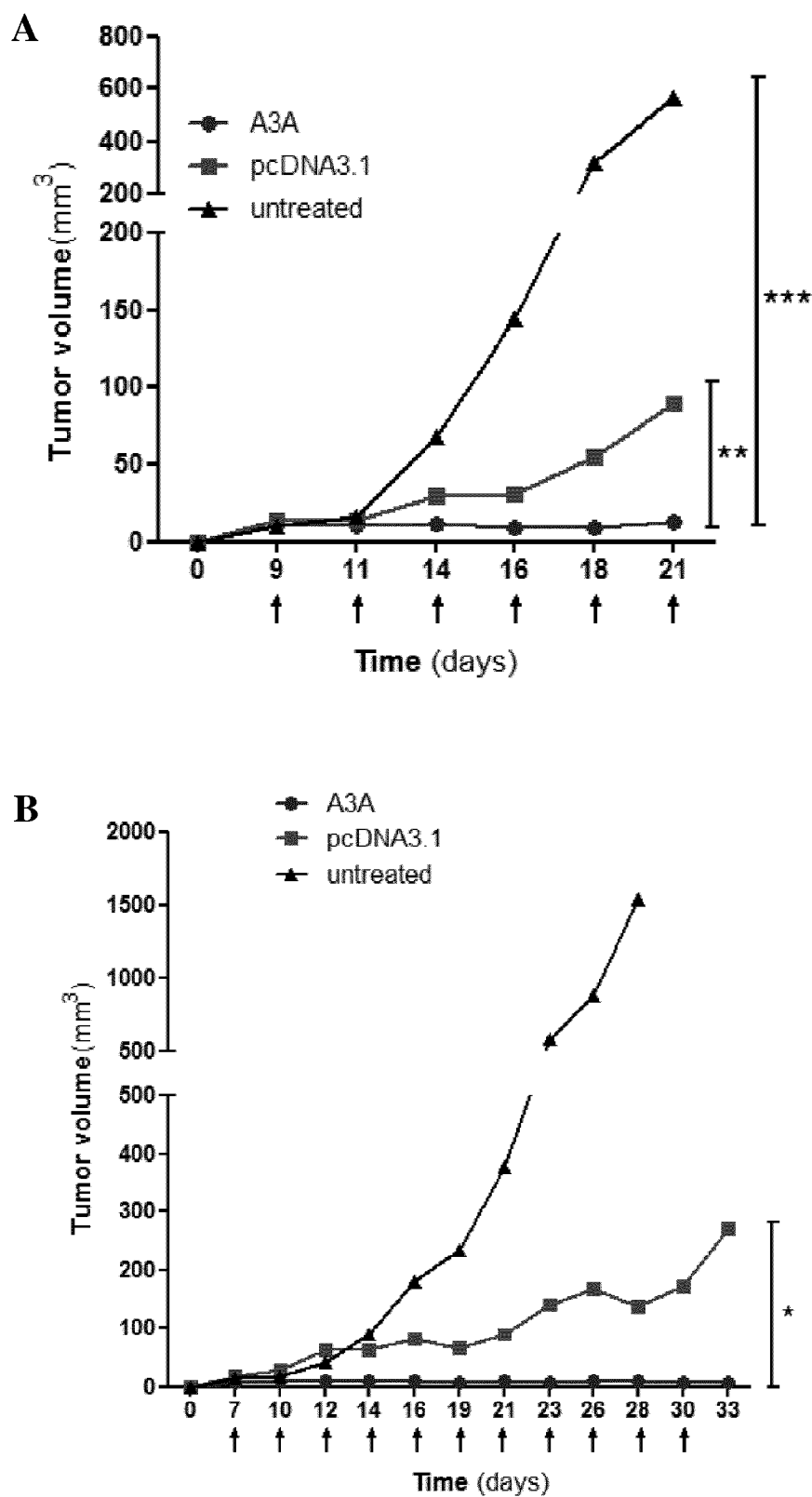
Figure 1:
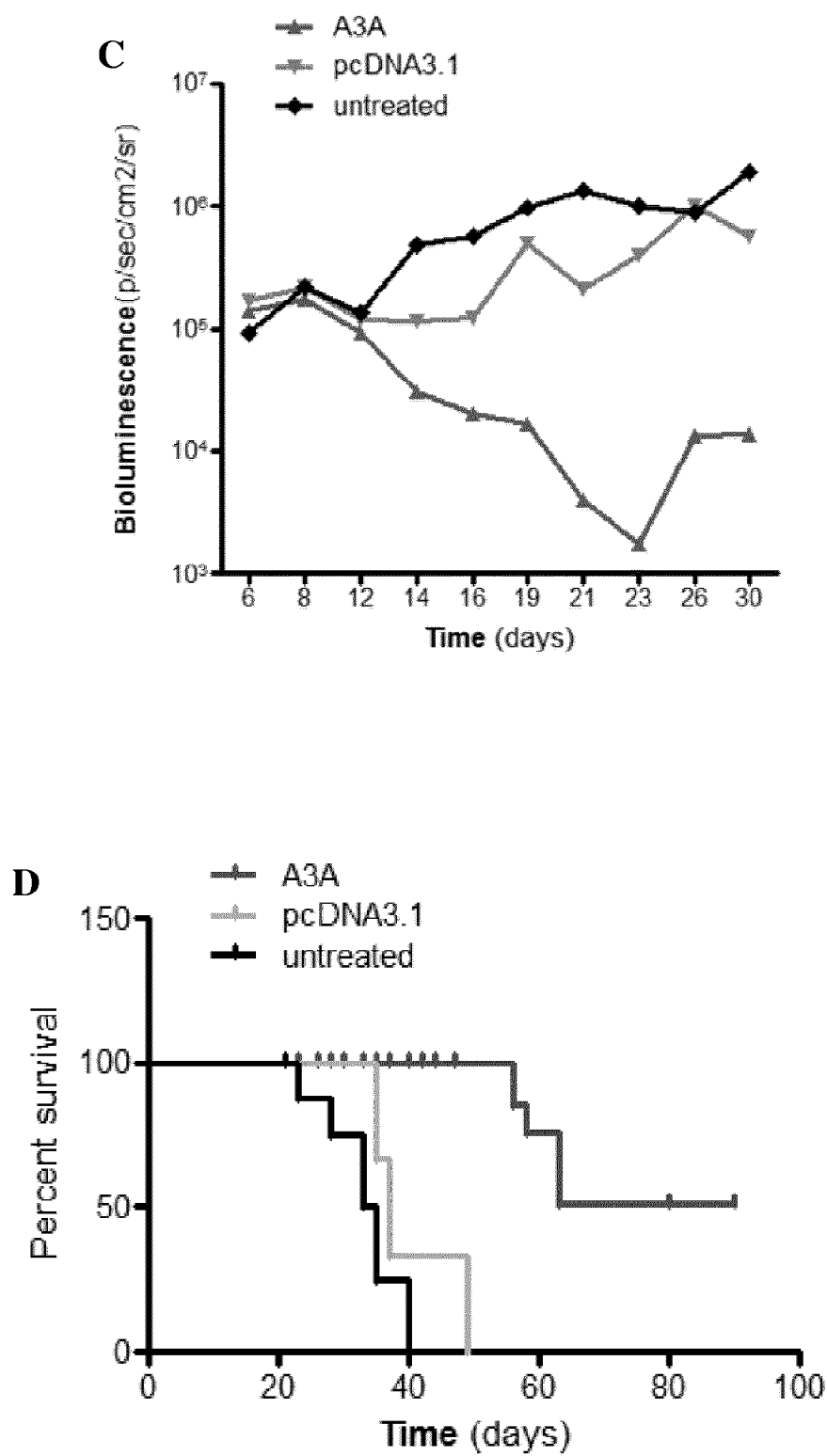

```
       1         10        20        30        40        50        60        70
       •         •         •         •         •         •         •         •
3A     MEASPASGPRHLMDPHIFTSNFNNG---IGRHKTYLCYEVERLDNGTSVLMDQHRGFLHNQAKNLLCGFYGRH
                 ****  ** ****     *************  **********  * ************
3Bc    ----------YLMDPDTFTFNFNNDPLVLRRRQTYLCYEVERLDNGTWVLMDQHMGFLCNEAKNLLCGFYGRH
                 •         •         •         •         •         •         •
                 190       200       210       220       230       240       250

80        90        100       110       120       130       140
           •         •         •         •         •         •         •
3A     AELRFLDLVPSLQLDPAQIYRVTWFISWSPCFSWGCAGEVRAFLQENTHVRLRIFAARIYDYDPLYKEAL
       *********************************************************************
3Bc    AELRFLDLVPSLQLDPAQIYRVTWFISWSPCFSWGCAGEVRAFLQENTHVRLRIFAARIYDYDPLYKEAL
           •         •         •         •         •         •         •
           260       270       280       290       300       310       320

150       160       170       180       190       199
           •         •         •         •         •         •
3A     QMLRDAGAQVSIMTYDEFKHCWDTFVDHQGCPFQPWDGLDEHSQALSGRLRAILQNQGN
       ******************  ******  ***********  ******************
3Bc    QMLRDAGAQVSIMTYDEFEYCWDTFVYRQGCPFQPWDGLEEHSQALSGRLRAILQNQGN
           •         •         •         •         •         •
           330       340       350       360       370       380
```

FIGURE 6

METHOD OF TREATING FIBROSARCOMA USING A NUCLEIC ACID SEQUENCE ENCODING APOBEC3A

CROSS-REFERENCE TO RELATED APPLICATIONS

This application is the U.S. National Phase of International Patent Application Serial No. PCT/EP2014/061516, filed on Jun. 3, 2014, which claims priority to European Patent Application No. EP 13305732.3, filed on Jun. 3, 2013.

The present invention relates to immunotherapy of cancers. More particularly the invention provides APOBEC3A encoding vectors for use in preventing or treating a tumor.

BACKGROUND OF THE INVENTION

APOBEC ("apolipoprotein B mRNA editing enzyme, catalytic polypeptide-like") is a family of evolutionary conserved proteins. Members of this family are C-to-U editing enzymes involving a distinctive zinc-finger catalytic domain. Some APOBEC proteins are made up of a single zinc-finger domain while others have two, referred to N- and C-terminal domains. The carboxy-terminal domain is functional for all but APOBEC3DE. The N-terminal domains of APOBEC3B, APOBEC3DE, APOBEC3F and APOBEC3G are non-functional. More specifically, the zinc finger cytidine deaminase domain and is essential for cytidine deamination.

U.S. patent application 2009/0260090 provides methods for preventing the occurrence or progression of a cancer or pre-cancer conditions associated with expression, or overexpression of APOBEC3 proteins.

Physiologically, expression of APOBEC3A is particularly well detected in cells of myeloid lineage and this is positively regulated by INF-α (Berger et al., 2011; Koning et al., 2009; Refsland et al., 2010).

However the true physiological functions of APOBEC3 proteins are not yet conclusively established.

Recently published data indicate that APOBEC3A is a particular deaminase which acts by equally efficient deamination of cytosine and 5-methylcytosine to uracil and methyluracil (thymidine) in single-stranded DNA (ssDNA) (Suspene et al., 2011; Wijesinghe and Bhagwat, 2012). Consequently APOBEC3A can trigger genetic and epigenetic modifications in extensively dividing cells. Uracil excision followed by abasic endonuclease cleavage of the DNA strand, leads to double strand breaks (DSBs) (Landry et al., 2011). DNA breaks are a potent signal for the initiation of DNA damage response leading to cell-cycle checkpoints. Failure to repair a single DSB prior to cell division may lead to prolonged cell cycle arrest, failure to undergo cell division and ultimately cell death. Cells that escape arrest and continue to divide with unrepaired breaks may eventually succumb to mitotic catastrophe (Hiom, 2010).

SUMMARY OF THE INVENTION

Departing from the prior art, the inventors now propose to use a nucleic acid that comprises a sequence encoding an APOBEC3A protein, in preventing or treating a solid tumor in a patient.

In a preferred embodiment, the sequence encodes wild-type APOBEC3A protein.

In another embodiment, the sequence encodes an APOBEC3A variant that shows at least 80%, preferably at least 90%, homology with APOBEC3A sequence shown in SEQ ID NO: 2.

The nucleic acid may preferably be in form of a plasmid or viral vector.

Advantageously, the delivery may be intratumorally. The nucleic acids may be introduced into tissues or host cells by any number of routes, including viral infection, microinjection, or fusion of vesicles.

Preferably the nucleic acid is intended for administration by electroporation.

LEGENDS TO THE DRAWINGS

FIGS. 1A to 1D are graphs showing that APOBEC3A (A3A) expression induces tumor cell death in vivo. Inhibition of tumor growth by APOBEC3A intratumoral electroporation into B16OVA and B16Luc tumors. The electroporation and tumor volume were assessed every 2-3 days. Black arrows indicate day of tumor electroporation (↑). The growing tumors implanted into dermal tissues were followed by measuring the length (a) and width (b) and the tumor volume (V) was calculated according to the formula $V = ab^2/2$.

A) C57BL/6J mice were inoculated subcutaneously (s.c.) with $2 \times 10^5$ B16OVA cells on day 0. The tumor bearing mice were divided into 3 groups (n=5) and electroporated intratumorally with APOBEC3A, pcDNA3.1 or untreated. Graph represents the mean tumor growth volume per group of mice studied, error bars are standard error of the mean (SEM) (*P=0.0001 APOBEC3A vs untreated, P=0.0009 APOBEC3A vs pcDNA3.1 Unpaired t test).

B) C57BL/6J mice (n=3-4) were injected s.c. with $2 \times 10^5$ B16Luc tumor cells and when tumor diameter reached 3 mm in diameter at day 7, they received the first electroporation. Graph represents the median tumor growth volume per group of mice studied (**P=0.0458 APOBEC3A vs pcDNA3.1 Unpaired t test).

C) Mean bioluminescence intensity of B16Luc tumors were measured before treatment and 2-3 times a week during treatment (n=3-4).

D) Survival of mice. Kaplan-Meier survival curves for C57BL/6J mice inoculated s.c. with $2 \times 10^5$ B16Luc cells. Groups of mice were followed for long-term survival (up to 80 days after initiation of the treatment).

Figure 2:
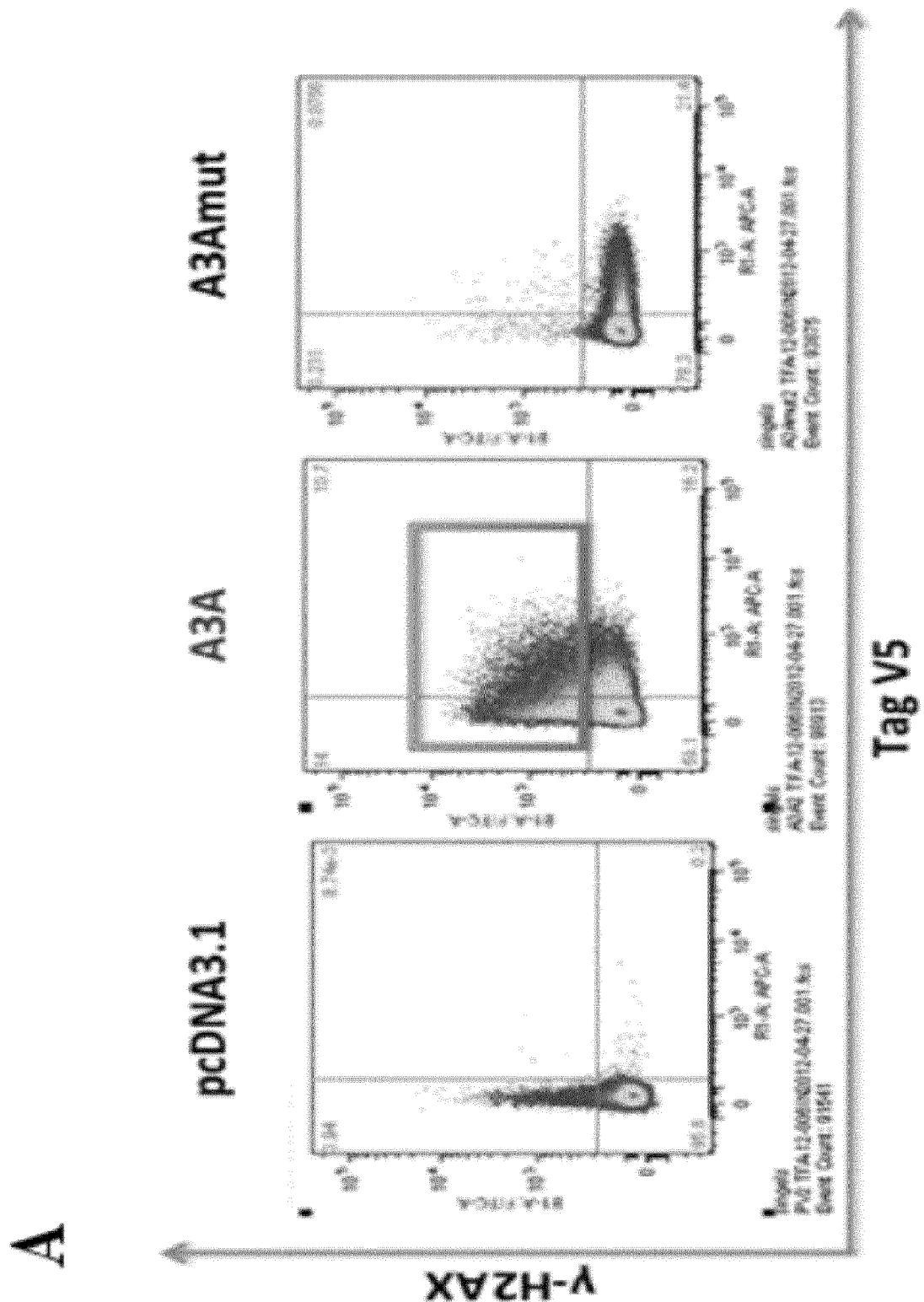
Figure 2:
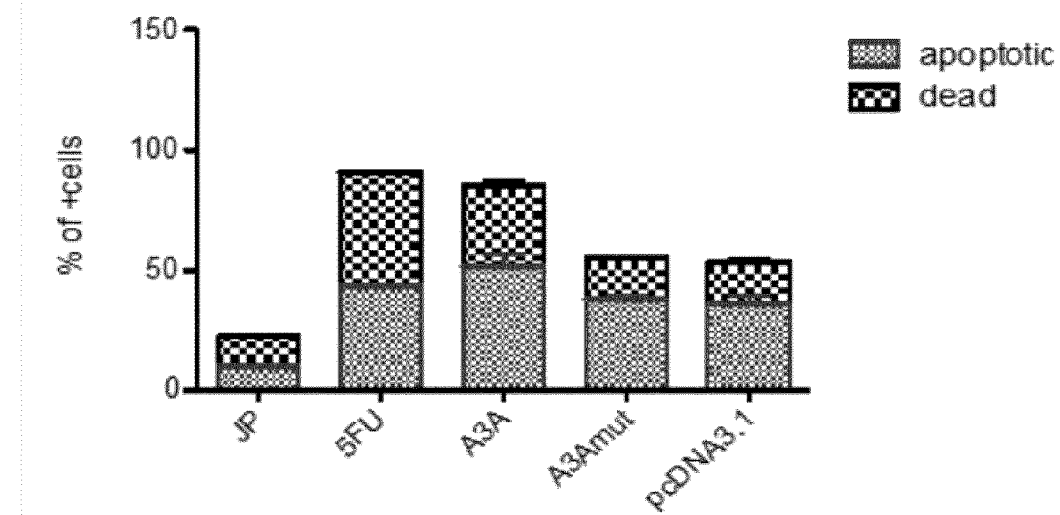

FIGS. 2A and 2B show in vivo analysis of APOBEC3A induced cell death.

A) APOBEC3A elicits DNA breaks in human melanoma M8G1 cells in vitro. M8G1 cells transfected with plasmids expressing A3A, A3A-P1S C101S cysteine mutant or pcDNA3.1 control plasmid were fixed 48 h post-transfection, stained with anti-tagV5 and gH2AX antibodies, and analyzed by flow cytometry.

B) APOBEC3A increases apoptosis and cell death in human melanoma M8G1 cells. M8G1 cells transfected with plasmids expressing A3A, A3A-P1S C101S cysteine mutant, pcDNA3.1 control plasmid or treated with 10 mg/ml 5-fluorouracil and transfection control cells (JP) were fixed 72 h post-transfection, stained with Annexin V antibody and propidium iodide, and analyzed by flow cytometry (mean of two experiments).

FIGS. 3A to 3D show that intratumoral electroporation of A3A induces DDR/DSB formation in Sarc2 tumor cells. HLA-A2DR1 mice were inoculated s.c. with $10^5$ Sarc2 cells.

(A) Black arrows indicate day of tumor electroporation (↑) with A3A plasmid. 2-3 mice in each group from two independent experiments were killed 3 weeks after tumor inoculation. The tumors were excised and tumor cells and tumor infiltrating lymphocytes (TIL) isolated. Graph represents the mean tumor growth volume per group of mice studied (n=3), (ns A3A vs untreated, p=0.34, Unpaired t test). 2-3 mice in each group from two independent experiments were sacrificed 3 weeks after tumor inoculation. The tumors were excised and tumor cells and tumor infiltrating lymphocytes (TILs) isolated.

Sarc2 tumor cells (B) and TILs (C) were counted under an optical microscope. Number of isolated Sarc2 cells decrease in tumors treated with A3A (B) (**P=0.0017 Unpaired t test). No significant difference was observed in number of isolated TILs (C) (ns. P=0.153, Unpaired t test).

(D) Sarc2 tumor cells were stained with γH2AX antibody and analyzed by flow cytometry. Increased level of activated DNA damage in fibrosarcoma tumors was observed after intratumoral electroporation of A3A (ns P=0.064, Unpaired t test).

Figure 4:
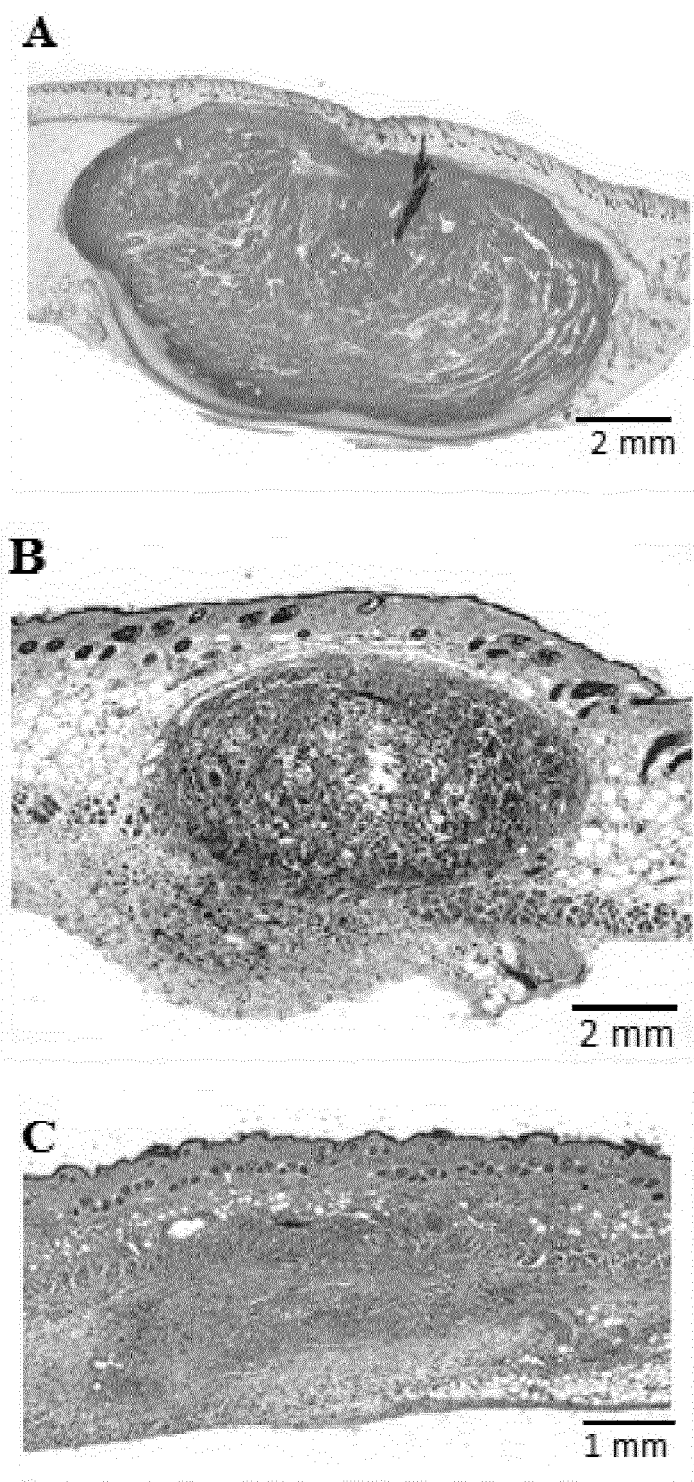

FIGS. 4A to 4C show that APOBEC3A overexpression induces B16OVA tumors regression.

Representative light microscope images of hematoxyline and eosin sections on tumors ectomized at day 22. Results from C57BL/6J mice injected with $2\times10^5$ B16OVA cells, treated as on FIG. 1A. A) untreated control group, B) pcDNA3.1, C) A3A treated.

Figure 5:
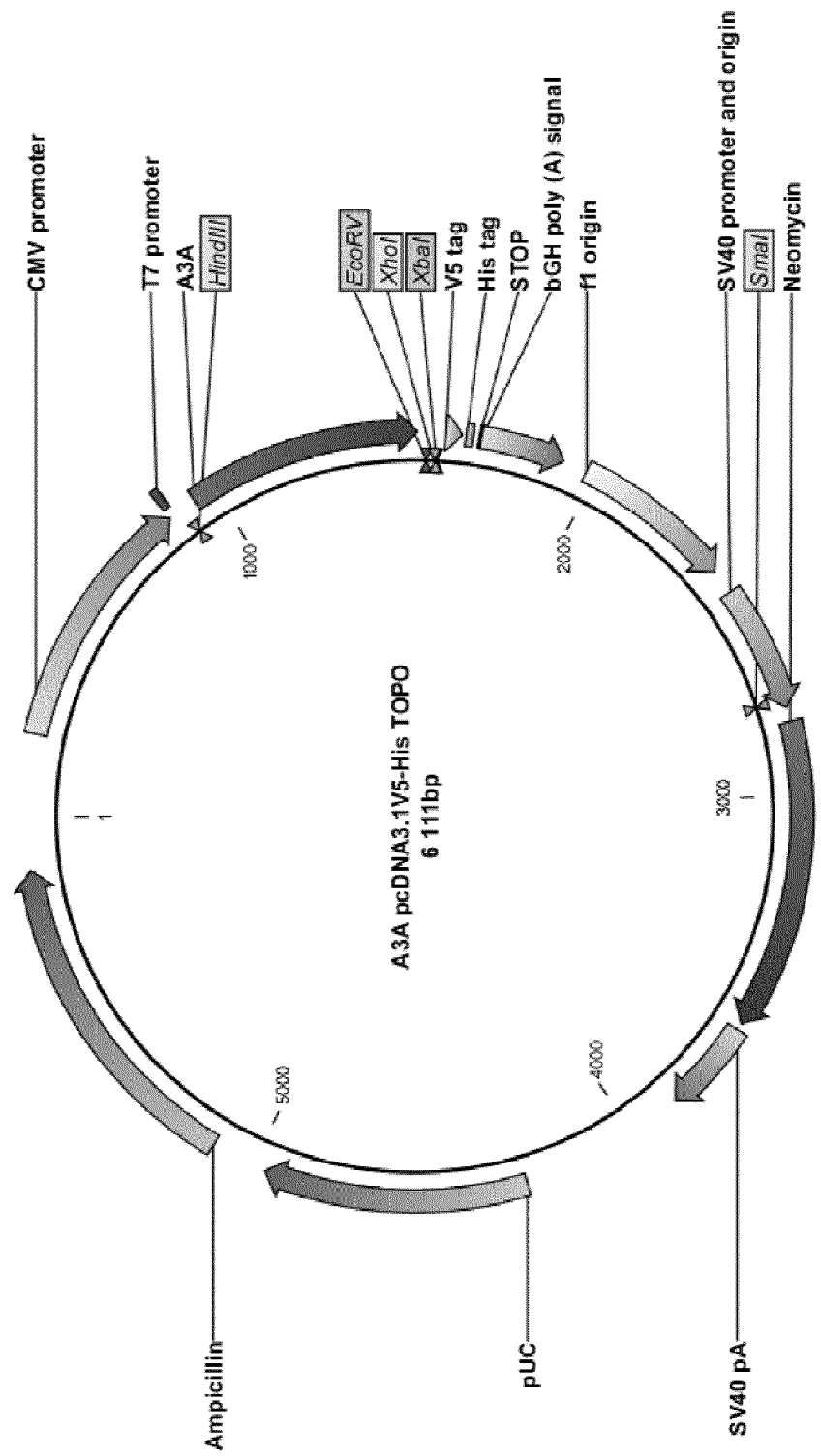

FIG. 5 shows a plasmid map of APOBEC3A cloned in pcDNA3.1D_V5-His-TOPO.

FIG. 6 shows a comparison of amino sequences of human APOBEC3A and the carboxy-terminal domain of APOBEC3B. Hyphens have been added to maximize sequence identity. Asterisks indicate amino acid identity. The numbering of each protein is that of the full length protein. The sequence identity is 91%.

DETAILED DESCRIPTION OF THE INVENTION

As shown in the below Experimental Section, the inventors observed a significant antitumor effect when administering an APOBEC3A encoding vector in preclinical models.

According to the invention, the injection of the nucleic acid encoding an APOBEC3A protein induces DNA damage response apoptosis of the tumor cells.

Without being linked by a mechanism, the inventors have good reason to believe that the tumor cell death they observed result from the action of expression of NKG2D ligands on the surface of cancer cells, which expression in turn is detected by cells of the innate (NK cells), transitional (γδ and NKT cells) and adaptive (CD8+ T cells).

Definitions

In the present invention, the term "APOBEC3" refers to a human APOBEC3 protein, more particularly an APOBEC3 protein expressed by any of the seven genes (A3A-A3H) of the human APOBEC3 locus. Preferably it is a "functional" APOBEC3, i.e. a APOBEC3 protein or isoform showing a catalytic activity of DNA or RNA editing.

A cDNA sequence of APOBEC3A has been described and is shown as SEQ ID NO: 1, and its corresponding amino acid sequence as SEQ ID NO: 2.

A cDNA sequence of APOBEC3B (long isoform) is shown as SEQ ID NO: 3, and its corresponding amino acid sequence as SEQ ID NO: 4.

In the present invention, the term "variant" refers to allelic variants, splicing variants, natural or artificial mutants, which are homologous to the APOBEC3 sequence of reference. The variant is "functional", in that it shows a catalytic activity of DNA or RNA editing.

Two amino acid sequences are "homologous", "substantially homologous" or "substantially similar" when one or more amino acid residue are replaced by a biologically similar residue or when greater than 80% of the amino acids are identical, or greater than about 90%, preferably greater than about 95%, are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs known in the art (BLAST, FASTA, etc.).

By "substituted" or "modified" the present invention includes those amino acids that have been altered or modified from naturally occurring amino acids.

In a particular embodiment, the sequence encodes a APOBEC3A variant that shows at least 80%, preferably at least 90%, still preferably at least 95%, or at least 98% homology with APOBEC3A sequence shown in SEQ ID NO:2.

It is also described APOBEC3B or variant that shows at least 80%, preferably at least 90%, still preferably at least 95%, or at least 98% homology with APOBEC3B sequence shown in SEQ ID NO:4.

Variants include proteins having a sequence that differs from wild-type APOBEC3 protein by one or several mutations (i.e. substitutions, deletions, insertions), still preferably one or several single point substitutions. For instance, a shortened APOBEC3A sequence could be used, e.g. by deleting several N-term or C-term amino acids, preferably one to four amino acids at the C-terminus of the sequence.

In a particular embodiment, the mutation or substitution impacts on the activity, or the level of activity, of the protein. The preferred variant protein is a mutant that shows a sequence identical to SEQ ID NO: 2 or NO: 4, except for one or several (e.g. two, three, or four) point mutations.

The variant may alternatively, or in addition, comprise conservative substitutions.

The term "conservative substitution" as used herein denotes the replacement of an amino acid residue by another, without altering the overall conformation and function of the peptide, including, but not limited to, replacement of an amino acid with one having similar properties (such as, for example, polarity, hydrogen bonding potential, acidic, basic, shape, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine.

The term "isolated polynucleotide" is defined as a polynucleotide removed from the environment in which it naturally occurs. For example, a naturally-occurring DNA molecule present in the genome of a living bacteria or as part of a gene bank is not isolated, but the same molecule separated from the remaining part of the bacterial genome, as a result of, e.g., a cloning event (amplification), is isolated. Typically, an isolated DNA molecule is free from DNA regions (e. g., coding regions) with which it is immediately contiguous at the 5' or 3' end, in the naturally occurring genome. Such isolated polynucleotides may be part of a vector or a composition and still be defined as isolated in that such a vector or composition is not part of the natural environment of such polynucleotide.

As used herein, the term "treatment" or "therapy" includes curative treatment. More particularly, curative treatment refers to any of the alleviation, amelioration and/or elimination, reduction and/or stabilization (e.g., failure to progress to more advanced stages) of a symptom, as well as delay in progression of the tumor or of a symptom thereof.

As used herein, the term "prevention" or "preventing" refers to the alleviation, amelioration and/or elimination, reduction and/or stabilization (e.g., failure to progress to more advanced stages) of a prodrome, i.e. any alteration or early symptom (or set of symptoms) that might indicate the start of a disease before specific symptoms occur. In a particular embodiment, the invention is intended for prevention of relapses.

The "patient" is any mammal, preferably any human being, regardless of the age, sex, and severity of the condition.

Nucleic Acid Constructs and Vectors

The nucleic acid of the invention is in isolated form,

Preferably, the nucleic acid is a genetic construct comprising a polynucleotide sequence encoding an APOBEC3 protein or a variant thereof, and regulatory sequences (such as a suitable promoter(s), enhancer(s), terminator(s), etc.) allowing the expression (e.g. transcription and translation) of the protein product in the host cell or host organism.

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting aspect, a genetic construct of the invention comprises i) at least one nucleic acid of the invention; operably connected to ii) one or more regulatory elements, such as a promoter and optionally a suitable terminator; and optionally also iii) one or more further elements of genetic constructs such as 3'- or 5'-UTR sequences, leader sequences, selection markers, expression markers/reporter genes, and/or elements that may facilitate or increase (the efficiency of) transformation or integration.

In a particular embodiment, the genetic construct can be prepared by digesting the nucleic acid polymer with a restriction endonuclease and cloning into a plasmid containing a promoter such as the SV40 promoter, the cytomegalovirus (CMV) promoter or enhancer, the Rous sarcoma virus (RSV) promoter or the Elongation Factor-1α (EF-1α). In a preferred embodiment, the APOBEC3 nucleic acid sequence is inserted into a pcDNA3.1 or pcDNA3.1DN5-His-TOPO expression plasmid.

Other vectors include retroviral vectors, lentivirus vectors, adenovirus vectors, vaccinia virus vectors, pox virus vectors and adenovirus-associated vectors, measles virus vectors.

Compositions can be prepared, comprising said nucleic acid or vector. The compositions can comprise a carrier or excipients that are suitable for administration in humans (i.e. non-toxic, and, if necessary, sterile). Such excipients include liquid, semisolid, or solid diluents that serve as pharmaceutical vehicles, isotonic agents, stabilizers, or any adjuvant.

Diluents can include water, saline, dextrose, ethanol, glycerol, and the like. Isotonic agents can include sodium chloride, dextrose, mannitol, sorbitol, and lactose, among others. Stabilizers include albumin, among others. Any adjuvant known in the art may be used in the composition, including oil-based adjuvants such as Freund's Complete Adjuvant and Freund's Incomplete Adjuvant, mycolate-based adjuvants, bacterial lipopolysaccharide (LPS), peptidoglycans, proteoglycans, aluminum hydroxide, saponin, DEAE-dextran, neutral oils (such as miglyol), vegetable oils (such as arachis oil), Pluronic® polyols.

The nucleic acid or composition can be administered directly or they can be packaged in liposomes or coated onto colloidal gold particles prior to administration. Techniques for packaging DNA vaccines into liposomes are known in the art, for example from Murray, 1991. Similarly, techniques for coating naked DNA onto gold particles are taught in Yang, 1992, and techniques for expression of proteins using viral vectors are found in Adolph, 1996.

The nucleic acid may be delivered at the tumor site, i.e. intratumorally or in the vicinity of the tumor, or intravenously. Alternatively the nucleic acid or composition may be administered intradermally, subcutaneously or intramuscularly. Other routes of delivery may be oral (tablet or pill form) and/or intrathecal delivery (Gold, 1997).

The nucleic acid may be locally delivered by direct injection or by use of an infusion pump. Preferably, the nucleic acid or composition is administered by injection or by gas driven particle bombardment. Jet injection may be used particularly useful for intra-muscular administration, as described by (Furth et al., 1992). The nucleic acids may be coated onto gold microparticles, and delivered by a particle bombardment device, or "gene gun" as described in the literature (see, for example, Tang et al. 1992), where gold microparticles are coated with the DNA, then bombarded into skin cells.

In a preferred embodiment of the present invention, administration comprises an electroporation step, also designated herein by the term "electrotransfer", in addition to the injection step (e.g. as described in Mir 2001, Sardesai and Weiner 2011). In a particular embodiment, the electrostimulation comprises first with a single pulse of High Voltage field strength of 1000 to 1500 V/cm and of duration of 10 μs to 1000 μs;

second, preferably after a defined lag time of e.g. at least 1000 ms, a single pulse of Low Voltage field strength of 50 to 250 V/cm, preferably 100 to 150 V/cm and of duration of between 300 and 800 ms.

The nucleic acids of the invention may be introduced into primary hematopoietic cells by using cell-type specific delivery of said nucleic acids complexed with antibody fragment protamine fusion proteins (Song et al., 2005). The cell delivery method may allow for systemic, cell-type specific, antibody-mediated delivery of the nucleic acid. The delivery methods for nucleic acids describe above may also use to delivery compositions as described above.

In still a preferred embodiment, the nucleic acid, which is preferably a DNA plasmid, is injected intratumorally by electrotransfer.

The dosage and regimen depend of the severity of the condition, and the weight and age of the patient. The nucleic acid or composition can be administered at a dosage of 0.01 to 2 mg, preferably from 0.1 to 10 mg. Preferably repeated doses of the nucleic acid or composition are administered. For instance, it can be administered at least once a day, or at least once or twice a week, during several weeks, e.g. from 1 to 12 weeks. In a particular embodiment, the nucleic acid may be administered at least once a day, during five days. In another particular embodiment, the nucleic acid may be administered every 3 or 7 days, and repeated, e.g. more than 5 times.

Prevention and Treatment of Tumors

The nucleic acid or composition as described above is useful in a method for preventing or treating a tumor in a patient.

A method for preventing or treating a tumor in a patient is described, which method comprises administering an effective amount of said nucleic acid or composition in a patient in need thereof. Said nucleic acid or composition is administered in an amount sufficient to induce immunogenic tumor cell death in the patient.

The tumor may be any undesired proliferation of cells, in particular a benign tumor or a malignant tumor, especially a cancer.

The cancer may be at any stage of development, including the metastatic stage. In particular, the immune response that is triggered by the "danger signals" emitted by cancer cells treated with APOBEC3A. The immune system uses professional antigen-presenting cells (APC) as sentinels of tissue damage. In the presence of danger signals, APC—such as dendritic cells, activated macrophages, and B cells—stimulate the T cell response to destroy metastatic cells.

The treatment of the invention, which involves expressing a self protein in situ, is not toxic toward the organism of the patient. So there is no side-effect, or fewer side effects than chemotherapy.

Preferably the tumor is a solid cancer or a carcinoma. The treatment of the invention advantageously inhibits solid tumor growth, e.g. by at least 80%. The invention further allows for multiple and unknown antigens to be targeted by both the innate and adaptive immune system. Another advantage over chemotherapy is that the plasmid DNA diffuses much less than a small molecule so limiting its effects to the site of application. According to that embodiment, the nucleic acid is preferably delivered at the tumor site, i.e. intratumorally or in the vicinity of the tumor.

In particular the tumor may be selected from the group consisting of melanoma, brain tumor such as glioblastoma, neuroblastoma and astrocytoma and carcinomas of the bladder, breast, cervix, colon, lung, especially non-small cell lung cancer (NSCLC), pancreas, prostate, head and neck cancer, or stomach cancer.

In another embodiment, the tumor may be a liquid tumor, e.g. a hematopoietic tumor or leukemia, such as a chronic lymphocytic leukemia, chronic myeloid leukemia, multiple myeloma, malignant myeloma, Hodgkin's disease.

In a particular embodiment, the treatment according to the invention may be combined with conventional therapy, including chemotherapy, radiotherapy or surgery. Combination with chemotherapeutic agents, immunomodulators, immune checkpoint blockers is thus encompassed.

Combinations with adjuvant immunomodulating molecules such GM-CSF or IL-2 are particularly useful.

The Figures and Examples illustrate the invention without limiting its scope.

EXAMPLES

Example 1: APOBEC3A Intratumoral Electroporation Suppresses Tumor Growth in Mice Summary:

The inventors hypothesized that ectopic expression of APOBEC3A in extensively dividing cancer cells can trigger immunogenic tumor cell death by expression of NKG2D ligands. To test this hypothesis APOBEC3A plasmid was electroporated intratumorally. The first treatment was administered when the tumor reached 2-3 mm in diameter. The treatment was repeated 6 times every 2-3 days. Early APOBEC3A treatment of B16OVA tumors resulted in massive tumor necrosis, 100% inhibition of tumor growth and prolonged mice survival.

1.1. Materials and Methods

Plasmid DNA Preparations

The purified A3A cDNA was inserted into the ampicillin-resistant plasmid vector pcDNA3.1N5-His-TOPO (Invitrogen), the size of the cloning vector including the insert is 6.11 kb (FIG. 5). A3A and control pcDNA3.1DN5-His-TOPO plasmids were obtained from Simon Wain-Hobson's laboratory, Institut Pasteur, Paris. Large-scale preparations of Endotoxin free, high quality plasmid were performed by RD Biotech Company (Besancon, France). Plasmids were resuspended in endotoxin-free PBS (Life Technologies).

Animals and Tumor Cell Lines

Female 7-week-old C57BL/6J mice were purchased from Janvier (Le Genest-Saint-Isle, France) and were used for the B16 melanoma model. Female and male 8- to 9-week-old HLA-A2DR1 mice providing from internal breading were used for the mouse Sarc2 fibrosarcoma. The mice had free access to food and water and were maintained in climate-controlled rooms at a 12-h light-dark cycle.

Mouse B16OVA melanoma cells encode the full-length chicken ovalbumin gene and were obtained from Olivier Adotévi (Immunology, Oncology Department UMR 1098 INSERM/EFS/UFC, Besancon, France). Mouse B16-F10 cells transfected to over-express luciferase (Caliper Life Sciences) were obtained from Marc Daëron (Molecular & Cellular Allergology, Institut Pasteur, Paris). Sarc2 cells, a mouse fibrosarcoma cell line derived from HLA-A2DR3 transgenic mice and was characterized in our laboratory.

All cell lines were cultured in Dulbecco's modified Eagle's medium (DMEM) supplemented with 10% fetal calf serum (FCS) and 1% penicillin/streptomycin. B16OVA cells were maintained with 500 µg/ml gentamycin 418 for ovalbumin selection.

Tumor Formation

The B16OVA and B16Luc tumors were established by subcutaneous injection of $2\times10^5$ cells into the right flank of C57BL/6J mice. For Sarc2 tumors formation, $5\times10^5$ cells were subcutaneously inoculated into the right flank of HLA-A2DR1 mice, and tumors were allowed to develop for about 9 days.

Cells were grown into round masses and EGT was started when inoculated tumors were 2-4 mm in diameter in the case of B16OVA and B16Luc tumors and 3-6 mm for Sarc2.

EGT Protocol and Measurements of Tumor Growth

C57BL/6J or HLA-A2DR1 mice were distributed to the various treatment and control groups for efficacy studies (n=10-15) and for immunohistochemistry (n=5). Animals bearing tumors outside the desired size range were excluded.

The procedure of electro-gene transfer (EGT) was previously described (Gehl, 2008; Mir et al., 2005). Briefly, mice were anesthetized with ketamine-xylazin using a mixture of Xylazin (2% Rompun, Bayer AG, Leverkusen, Germany) and Ketamine (8% Imalgen 1000, Merial, Lyon, France) in PBS. Predetermined quantity of 100 µg plasmid in 50 µl of Endotoxin free PBS was percutaneously injected into the B16OVA, B16Luc or Sarc2 tumors, using a 25-gauge insulin syringe. Good contact of the electrodes with the tumor tissue was produced using electrocardiography paste (Uni'gel US, Asept Inmed, France). Electric pulses (HV=1400 V/cm, 1

Hz, 100 μs, 1 pulse, 1000 ms break; LV=140 V/cm, 1 Hz, 400 ms, 1 pulse) were generated with an electroporator (IGEA, CLIPORATOR Italy) fitted with a non-invasive plate electrode (0.6 cm in diameter). Immediately after the DNA injection, electrodes were positioned around the tumors and electric pulses were administered. In the case of B16OVA tumor, EGT was administered to tumor-bearing mice either five times. In the case of B16Luc tumor, EGT was administered eleven times. The tumor size was measured with caliper and the volume was estimated as a $V=ab^2/2$, where (a) is the larger diameter and (b) is the smaller diameter (Tomayko and Reynolds, 1989; Wakabayashi et al., 2008). Average tumor volumes on day 21 of each experimental series were compared using unpaired t tests; values of p 0.05 were considered significant.

For survival analysis tumor size was monitored using a caliper three times weekly until the tumor reached around 1,500-2,000 mm$^3$ in size or until the animal died. Tumor volumes were calculated as described above. Mice were weighed three times a week until the end of the experiment.

Bioluminescence Imaging

To image bioluminescence, mice were injected with 0.15 mg/g luciferin (Promega, France) intraperitoneally at 20 mg/ml. Five minutes later they were anesthetized with 2-3% isoflurane (Attane™ Isoflurane, JD Medical Dist. Co., Inc) delivered in 100% oxygen at a flow rate of 0.8 liter/min and imaged using an IVIS Lumina (Caliper Life Sciences). The results were analyzed using Living Image software (Caliper Life Sciences).

Tumor Sampling and Hematoxylin and Eosin (H&E) Staining

Mice were sacrificed by $CO_2$ inhalation. Tumors and surrounding tissues were taken after skin incision using scissors and forceps. Tumors were fixed in JB fixative (zinc acetate 0.5%, zinc chloride 0.05%, and calcium acetate 0.05% in Tris-HCl buffer, pH7) for 48 hours, dehydrated in ethanol, then embedded in low-melting point paraffin (Polyethylene Glycol Distearate; Sigma-Aldrich, St Louis, USA). 5 μm thick paraffin sections were performed using SuperfrostPlus® slides (Fisher Bioblock Scientific, Illkirch, France), deparaffinized in absolute ethanol, air dried, and routinely stained with hematoxylin-eosin. Slides were counterstained with Gill's Hematoxylin (DAKO, Courtaboeuf, France) and mounted with Immunomount (SHANDON, Eragny, France). Slides were visualized by transmission light microscopy.

Tumor Preparations

Sarc2 tumors were cut with fine scissor into small pieces and placed in 10 ml Hank's Balanced Salt Solution (HBSS, Invitrogen) containing 10 mg collagenase (grade IV; Sigma-Aldrich), 0.01 mg hyaluronidase (Sigma-Aldrich), and 1 mg DNase (Sigma-Aldrich). After 1.5 hours incubation on a rocking platform at 37° C., the pellet was resuspended in DMEM (Invitrogen) and passed through a sterile 70 μM cell strainer (BD, Falcon). The resulting cell suspension was washed once in HBSS, resuspended in 5 ml 33% Percoll (in HBSS) to separate tumor cells from lymphoid cells and placed in a sterile 15 ml conical tube, which was centrifuged for 20 min at 2300 rpm at room temperature. The upper-layer (lymphoid cells) and supernatant was removed.

Cell Culture and Transient Transfection

M8G1 cells were obtained from Edgardo Carosella laboratory (Saint-Louis Hospital, Paris, France). Cells were cultured in Dulbecco's modified Eagle's medium (DMEM) supplemented with 10% heat-inactivated fetal calf serum (PAA) and 1% penicillin/streptomycin and 50 μg/ml hygromycin B. Cells were grown as monolayers in 75 cm$^2$ flasks at 37° C. in a humidified atmosphere containing 5% $CO_2$. The cells were grown to 80% confluence on the day of transfection. $7\times10^5$ M8G1 cells were seeded in six-well tissue culture plates and incubated for 24 h. The A3A, A3A-P1S C101S cysteine mutant, pcDNA3.1 control plasmid were transfected into target cells using JetPrime (Polyplus-transfection Inc., France) or TurboFect (Fermentas, UK) cationic polymer transfection reagent. Cells treated with 10 mg/ml 5-fluorouracil (Sigma-Aldrich) served as positive control. After 48-72 hours, cells were harvested and analyzed for DSBs and apoptosis.

DSBs Detection

At 48 h post-transfection floating and adherent cells were collected, washed with PBS, fixed in 4% ice-cold paraformaldehyde for 20 min and permeabilized in BD Perm-Wash buffer (BD Cytofix/Cytoperm Fixation/Permeabilization kit) for 15 min, at room temperature. Cells were incubated for 1 hour with 1:500 diluted mouse anti-V5 antibody (Invitrogen). After one wash with BD Perm/Wash buffer cells were stained 1 hour with 1:2000 diluted goat anti-mouse IgG-Alexa Fluor 633 secondary antibody (Invitrogen). Then cells were washed and incubated for 1 hour with 1:40 diluted Alexa Fluor 488-conjugated rabbit monoclonal γH2AX (20E3) antibody (Cell Signaling). All incubation steps were performed on ice. Data were acquired with MACS Quant flow cytometer (Miltenyi Biotec) and analyzed using FlowJo Software (Tree Star, Inc.). A total of 10,000 events were collected for each sample. For DSBs detection in vivo, Sarc2 tumor cells were fixed, permeabilized and stained with Alexa Fluor 488-conjugated rabbit monoclonal γH2AX (20E3) antibody (Cell Signaling) as described above.

Determination of Cell Death and Apoptosis In Vitro

At 72 h of after transfection, M8G1 cells were collected, washed with PBS and stained using the Alexa Fluor® 488 annexin V/Dead Cell Apoptosis Kit with Alexa® Fluor 488 annexin V and PI for Flow Cytometry Kit (Invitrogen, V13245) according to the manufacturer's instructions. Cells treated with 10 mg/ml 5-fluorouracil (Sigma) served as positive control. Cells were analyzed by flow cytometry on the MACS Quant flow cytometer (Miltenyi Biotec) and analyzed using FlowJo Software (Tree Star, Inc.). A minimum of 90,000 events were collected for each sample.

1.2. Results

Intratumoral A3A treatment leads to a significant inhibition of tumor growth and prolongs survival time of B16 melanoma bearing mice The weakly immunogenic tumor cell lines were used to evaluate whether constitutively activated A3A is a valid molecular target for killing or blocking tumor cell growth specifically. Intratumoral gene delivery in vivo by electroporation has been reported previously (Cemazar et al., 2002; Pavlin et al., 2011; Rols et al., 1998). The efficacy of electrogene transfer into 2 to 8 mm in diameter B16OVA tumors was determined by measure of luciferase bioluminescence intensity in vivo. 100 μg of plasmid coding luciferase gene were electroporated into tumor nodule. Intratumoral gene transfer was dependent on tumor diameter. The optimal electroporation conditions were obtained for small tumors (3-4 mm in diameter). The expression of luciferase gene was strong and constant one week after plasmid electroporation and luciferase expression was still present at 3-4 weeks post electroporation (data not shown).

To test inhibition of tumor growth by intratumoral A3A electroporation, $2\times10^5$ B16OVA cells were injected subcutaneously in the right flank of C57BL/6J mice. The initial electroporation was performed at day 9 when the tumor reached 2-3 mm in diameter. The 4 subsequent administrations were performed every 2-3 days. Intratumoral A3A gene transfer into nascent tumors induces statistically significant therapeutic effect in mice (pcDNA3.1 group n=5, A3A group n=10 and untreated group n=10) (FIG. 1A). Tumor growth was already reduced by day 5 post treatment in animals receiving A3A, compared with the control plasmid group (Unpaired t test P value=0.0014). The tumor growth was still very significantly inhibited at the end of 14 day following the treatment. pcDNA3.1 treated mice developed large tumor burdens by day 21 of tumor growth. A 23 fold reduction in tumor size was observed in the group treated with A3A as compared with that of pcDNA3.1 control group.

Optical bioimaging was used in vivo to track the amount of dying tumor tissue after A3A treatment. The same experimental conditions as described above were used to treat B16Luc mouse melanoma nodules stably expressing luciferase gene (n=3-4 mice per group). Bioluminescent tumors were electroporated with A3A or pcDNA3.1 control plasmid. The repeated electroporation of A3A plasmid DNA induces significant suppression of tumor growth (FIG. 1B). Bioluminescence intensity showed acute decrease after A3A electroporation at day 16 (FIG. 1C). As expected, bioluminescence intensity of the non-electroporated and pcDNA3.1 treated tumors increased over time. The volume of tumors treated with A3A was significantly different at day 33 post tumor cells injection than controls treated with pcDNA3.1 plasmid (P=0.0458).

To determine whether the tumor growth inhibition was constant and whether the survival was prolonged, after 11 electroporations (day 30) the treatment was stopped. Tumors were eradicated in 75% of the animals treated with A3A, and their survival was prolonged beyond 80 days, compared with the control untreated mice, which died by day 37 after tumor cell inoculation (FIG. 1D).

A3A Expression Induces DNA Damage Response Apoptosis In Vitro in M8G1 Human Melanoma Cell Line Expression of APOBEC3A leads to induction of DNA breaks, activation of damage responses in a deaminase-dependent manner and induces G1/S-phase cell-cycle arrest (Landry et al., 2011). DSBs elicit histone H2AX phosphorylation at serine 139, named γH2AX (Bonner et al., 2008), which is required for DNA damage signal amplification and accumulation of numerous DDR proteins at DSBs sites.

To evaluate tumor cell DNA integrity and viability after transfection of A3A, the human melanoma cell line M8 was transfected with plasmid coding A3A, A3A cysteine catalytic mutant (A3A P1SC101S) and pcDNA3.1 control plasmid and analyzed by flow cytometry. M8G1 tumor cells expressed A3A showed a strong activation of DDR confirmed by staining with an antibody against γH2AX. The phosphorylation of histone γH2AX was highly specific for catalytic activity of A3A as compared with A3A cysteine mutant and pcDNA3.1 control plasmid (FIG. 2A). Apoptosis and cell death of transfected cells were examined by propidium iodide and Annexin V staining and flow cytometry analysis (FIG. 2B). Induction of apoptosis and cell death after 48-72 h of transfection was comparable with positive control 5-fluorouracil treatment, which is a potent drug, used to treat several types of cancer including colon, rectum, head and neck cancers. These results demonstrate that overexpression of A3A can induce DNA damage response apoptosis in human melanoma cells.

A3A Expression Induces DSB In Vivo

Figure 3:
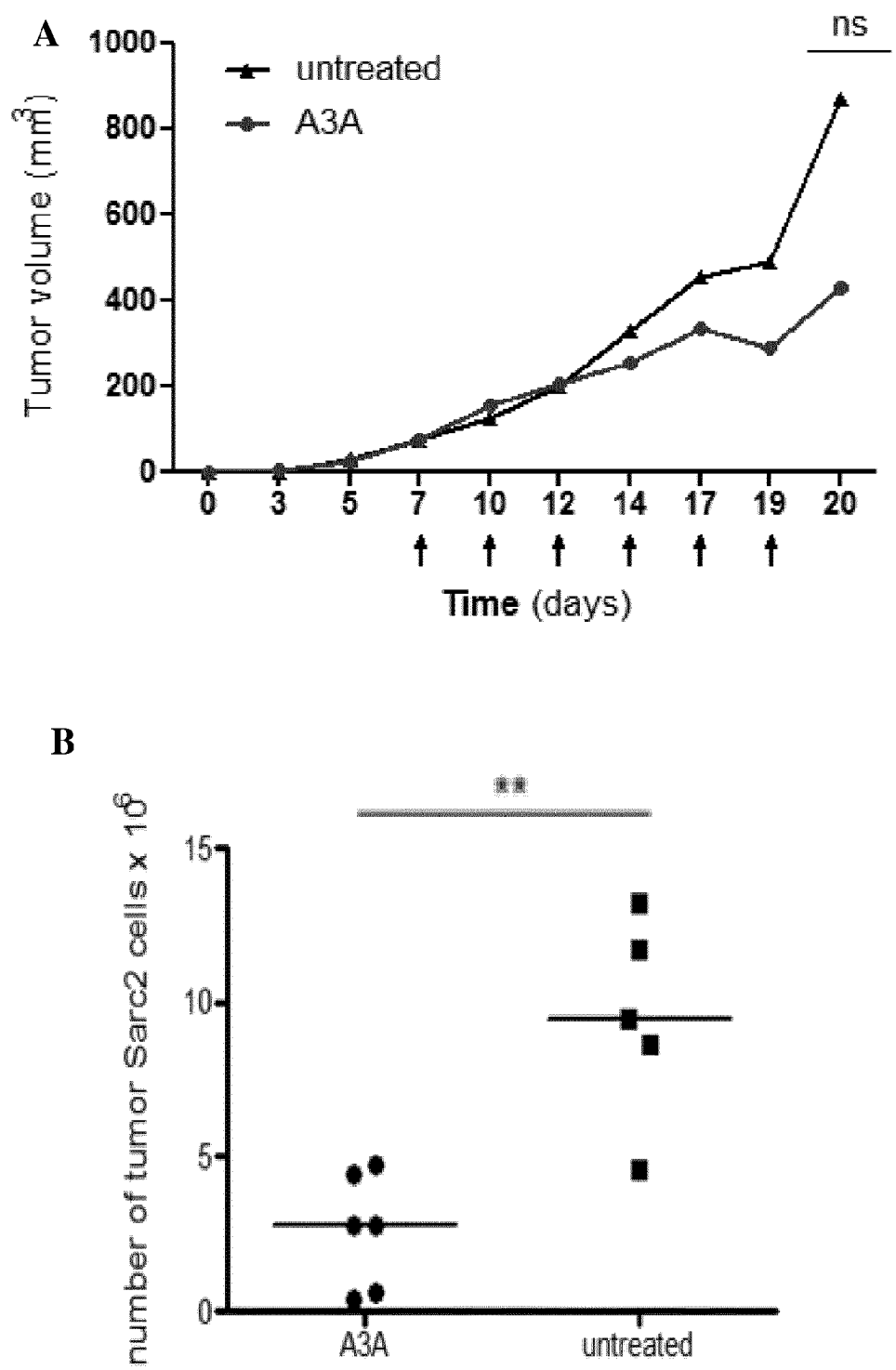
Figure 3:
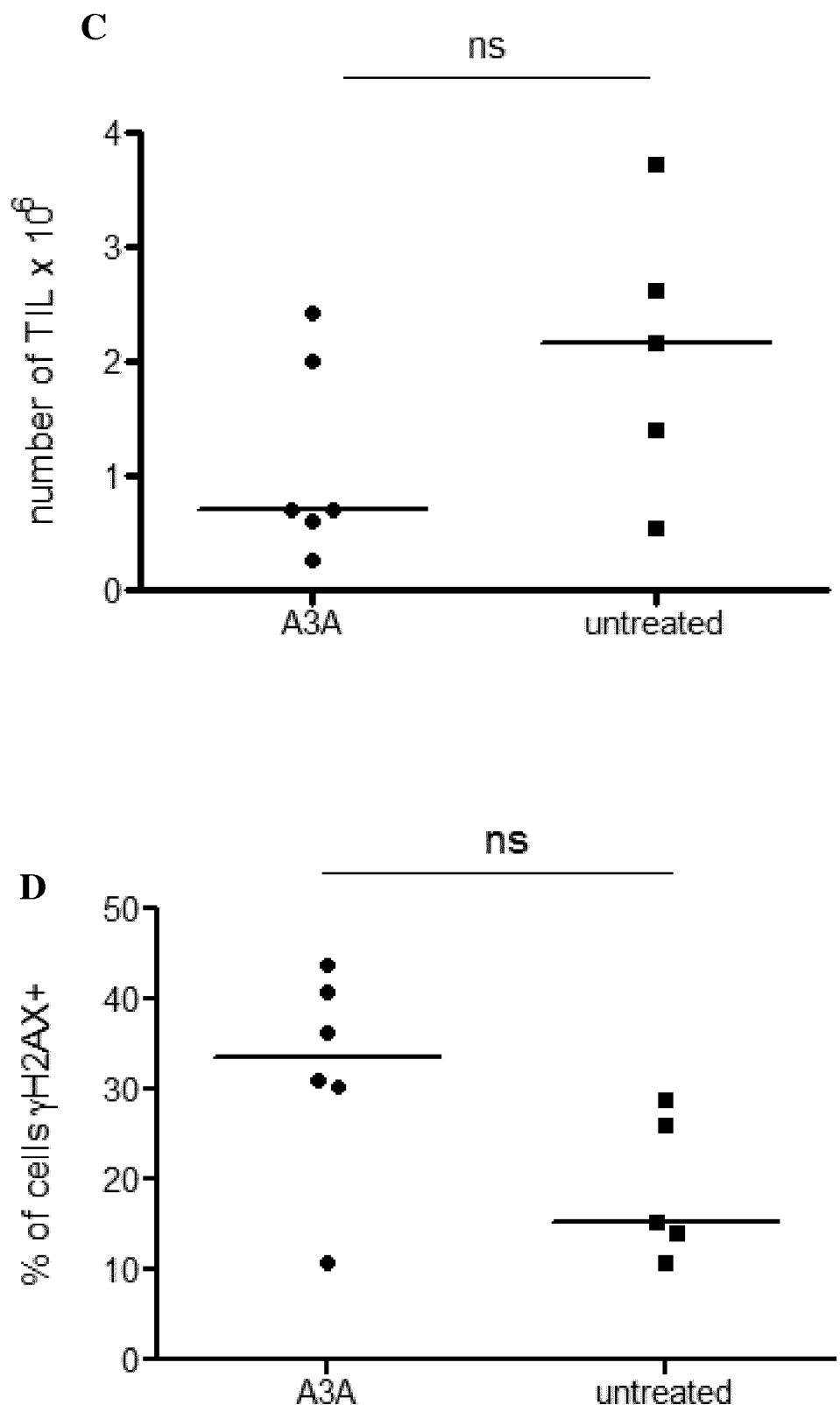

The inventors have then examined induction of DSB in vivo after intratumoral A3A gene transfer therapy. For that purpose an antibody directed against γH2AX was employed. This antibody is a sensitive marker for DNA double-strand breaks (DSBs) before and after cancer therapy as a biodosimeter of genotoxic effects of drugs or radiation (Nakamura et al., 2010; Redon et al., 2010). The A3A encoding plasmid was electroporated into extensively dividing fibrosarcoma Sarc2 tumors (HLA-A2DR3) inoculated in transgenic HLA-A2DR1 mice model. The electroporation was performed when the tumors reached 4-5 mm in diameter. The treatment was repeated five times every 2-3 days. Consequently tumors treated with A3A represented reduced tumor volume at day 21 as compared with untreated control Sarc2 tumors. After extraction and dissociation of the tumor, cells were counted under an optical microscope, stained with γH2AX antibody and analyzed by flow cytometry. Number of isolated tumor Sarc2 cells was highly correlated with the final tumor size reduction (FIG. 3A). We have detected significantly increased γH2AX level in the Sarc2 tumor cells isolated from mice treated with A3A (FIG. 3B, P value=0.0057 Unpaired t test). Only one of six treated mice represented low level of γH2AX in isolated Sarc2 tumor cells and it was resistant to A3A treatment (tumor growth similar to untreated control group, data not shown). These results suggest that intratumoral expression of A3A induces a strong DNA damage response in vivo in Sarc2 tumor cells.

Histology

To characterize some of the factors involved in the efficient tumor growth inhibition after A3A electroporation, tumors were ectomized at the day 21 post tumor cells injection. Histological analysis based on HE-staining showed massive tumor necrosis and complete B16OVA tumor eradication in 80% of A3A treated mice after 5 consecutive electroporations. All mice treated with control plasmid developed large tumor burdens (FIG. 4A-C). This demonstrates that A3A intratumoral electroporation can inhibit B16OVA tumor cells proliferation in vivo leading to complete tumor eradication.

CONCLUSION

Repeated electroporation of tumors with plasmid DNA coding A3A eradicates completely nascent tumors in 80-90% of mice, results in a significant increase in the survival of the A3A treated mice and induces significant tumor growth inhibition in well-established mouse melanoma and fibrosarcoma tumors. These results demonstrate that A3A plasmid DNA delivery by electroporation results in specific and effective anti-cancer therapy proving a good therapeutic significance of A3A as compared with control empty vector.

REFERENCES

Adolph, K. 1996 ed. "Viral Genome Methods" CRC Press, Florida

Berger, G., Durand, S., Fargier, G., Nguyen, X. N., Cordeil, S., Bouaziz, S., Muriaux, D., Darlix, J. L., and Cimarelli, A. (2011). APOBEC3A is a specific inhibitor of the early phases of HIV-1 infection in myeloid cells. PLoS Pathogens 7, e1002221.

Bonner, W. M., Redon, C. E., Dickey, J. S., Nakamura, A. J., Sedelnikova, O. A., Solier, S., and Pommier, Y. (2008). Gamma H2AX and cancer. Nature Reviews Cancer 8, 957-967.

Cemazar, M., Sersa, G., Wilson, J., Tozer, G. M., Hart, S. L., Grosel, A., and Dachs, G. U. (2002). Effective gene transfer to solid tumors using different nonviral gene delivery techniques: electroporation, liposomes, and integrin-targeted vector. Cancer Gene Therapy 9, 399-406

Furth, P. A., Shamay, A., Wall, R. J., and Hennighausen, L. (1992). Gene transfer into somatic tissues by jet injection. Analytical Biochemistry 205, 365-368.

Gehl, J. (2008). Electroporation for drug and gene delivery in the clinic: doctors go electric. Methods in Molecular Biology 423, 351-359.

Gold, B. G. (1997). Axonal regeneration of sensory nerves is delayed by continuous intrathecal infusion of nerve growth factor. Neuroscience 76, 1153-1158.

Hiom, K. (2010). Coping with DNA double strand breaks. DNA Repair 9, 1256-1263.

Koning, F. A., Newman, E. N., Kim, E. Y., Kunstman, K. J., Wolinsky, S. M., and Malim, M. H. (2009). Defining APOBEC3 expression patterns in human tissues and hematopoietic cell subsets. Journal of Virology 83, 9474-9485.

Landry, S., Narvaiza, I., Linfesty, D. C., and Weitzman, M. D. (2011). APOBEC3A can activate the DNA damage response and cause cell-cycle arrest. EMBO Reports 12, 444-450.

Mir, L. M. (2001). Therapeutic perspectives of in vivo cell electropermeabilization. Bioelectrochemistry 53, 1-10.

Mir, L. M., Moller, P. H., Andre, F., and Gehl, J. (2005). Electric pulse-mediated gene delivery to various animal tissues. Advances in Genetics 54, 83-114.

Murray, 1991, ed. "Gene Transfer and Expression Protocols" Humana Pres, Clifton, N.J.

Nakamura, A. J., Redon, C. E., and Bonner, W. M. (2010). gammaH2AX: Applications for the evaluation of telomerase-based cancer therapy. Cell Cycle 9, 3385-3386.

Pavlin, D., Cemazar, M., Cor, A., Sersa, G., Pogacnik, A., and Tozon, N. (2011). Electrogene therapy with interleukin-12 in canine mast cell tumors. Radiology and Oncology 45, 31-39.

Redon, C. E., Nakamura, A. J., Gouliaeva, K., Rahman, A., Blakely, W. F., and Bonner, W. M. (2010). The use of gamma-H2AX as a biodosimeter for total-body radiation exposure in non-human primates. PLoS One 5, e15544.

Refsland, E. W., Stenglein, M. D., Shindo, K., Albin, J. S., Brown, W. L., and Harris, R. S. (2010). Quantitative profiling of the full APOBEC3 mRNA repertoire in lymphocytes and tissues: implications for HIV-1 restriction. Nucleic Acids Research 38, 4274-4284.

Rols, M. P., Delteil, C., Golzio, M., Dumond, P., Cros, S., and Teissie, J. (1998). In vivo electrically mediated protein and gene transfer in murine melanoma. Nature Biotechnology 16, 168-171.

Song, E., P. Zhu, Lee, S. K. Chowdhury, D., Kussman, S., Dykxhoorn, D. M., Feng, Y., Palliser, D., Weiner, D. B., Shankar, P., Marasco, W. A., Lieberman, J. et al. (2005). "Antibody mediated in vivo delivery of small interfering RNAs via cell-surface receptors." Nature Biotechnology 23(6): 709-717.

Suspene, R., Aynaud, M. M., Guetard, D., Henry, M., Eckhoff, G., Marchio, A., Pineau, P., Dejean, A., Vartanian, J. P., and Wain-Hobson, S. (2011). Somatic hypermutation of human mitochondrial and nuclear DNA by APOBEC3 cytidine deaminases, a pathway for DNA catabolism. Proceedings of the National Academy of Sciences USA 108, 4858-4863.

Tang, D. C., DeVit, M., and Johnston, S. A. (1992). Genetic immunization is a simple method for eliciting an immune response. Nature 356, 152-154.

Tomayko, M. M., and Reynolds, C. P. (1989). Determination of subcutaneous tumor size in athymic (nude) mice. Cancer Chemotherapy and Pharmacology 24, 148-154.

Wakabayashi, A., Nakagawa, Y., Shimizu, M., Moriya, K., Nishiyama, Y., and Takahashi, H. (2008). Suppression of an already established tumor growing through activated mucosal CTLs induced by oral administration of tumor antigen with cholera toxin. Journal of Immunology 180, 4000-4010.

Wijesinghe, P., and Bhagwat, A. S. (2012). Efficient deamination of 5-methylcytosines in DNA by human APOBEC3A, but not by AID or APOBEC3G. Nucleic Acids Research 40, 9206-9217.

Yang, 1992, "Gene transfer into mammalian somatic cells in vivo", Critical Reviews in Biotechnology 12: 335-356

The invention claimed is:

1. A method for treating a fibrosarcoma in a mammal, comprising injecting a nucleic acid molecule encoding an APOBEC3A protein into a fibrosarcoma tumor in the mammal such that the tumor growth is inhibited, wherein the APOBEC3A protein comprises the amino acid sequence of SEQ ID NO: 2.

2. The method according to claim 1, wherein the nucleic acid molecule is in a form of a plasmid or viral vector.

3. The method according to claim 1, wherein the nucleic acid molecule is injected in combination with a chemotherapeutic agent, an immunomodulator, an immune checkpoint blocker or radiotherapy.

4. The method according to claim 1, wherein the nucleic acid molecule is injected in an amount which induces DNA damage and in the fibrosarcoma tumor.

5. The method of claim 1, wherein the mammal is a human.

6. The method of claim 1, wherein the nucleic acid molecule is injected by intratumoral electroporation.

* * * * *

SEQUENCE LISTING

```
<160> NUMBER OF SEQ ID NOS: 4

<210> SEQ ID NO 1
<211> LENGTH: 1444
<212> TYPE: DNA
<213> ORGANISM: Homo sapiens
<220> FEATURE:
<221> NAME/KEY: CDS
<222> LOCATION: (171)..(770)

<400> SEQUENCE: 1
ggagaagggg tggggcaggg tatcgctgac tcagcagctt ccaggttgct ctgatgatat      60
attaaggctc ctgaatccta agagaatgtt ggtgaagatc ttaacaccac gccttgagca     120
agtcgcaaga gcgggaggac acagaccagg aaccgagaag ggacaagcac atg gaa       176
                                                        Met Glu
                                                          1 gcc agc cca gca tcc ggg ccc aga cac ttg atg gat cca cac ata ttc      224
Ala Ser Pro Ala Ser Gly Pro Arg His Leu Met Asp Pro His Ile Phe
    5                   10                  15 act tcc aac ttt aac aat ggc att gga agg cat aag acc tac ctg tgc      272
Thr Ser Asn Phe Asn Asn Gly Ile Gly Arg His Lys Thr Tyr Leu Cys
 20                  25                  30
```

| | | | | | | | | | | | | | | | | |
|---|---|---|---|---|---|---|---|---|---|---|---|---|---|---|---|---|
| tac | gaa | gtg | gag | cgc | ctg | gac | aat | ggc | acc | tcg | gtc | aag | atg | gac | cag | 320 |
| Tyr | Glu | Val | Glu | Arg | Leu | Asp | Asn | Gly | Thr | Ser | Val | Lys | Met | Asp | Gln | |
| 35 | | | | 40 | | | | | 45 | | | | | 50 | | |

| | | | | | | | | | | | | | | | | |
|---|---|---|---|---|---|---|---|---|---|---|---|---|---|---|---|---|
| cac | agg | ggc | ttt | cta | cac | aac | cag | gct | aag | aat | ctt | ctc | tgt | ggc | ttt | 368 |
| His | Arg | Gly | Phe | Leu | His | Asn | Gln | Ala | Lys | Asn | Leu | Leu | Cys | Gly | Phe | |
| | | | | 55 | | | | | 60 | | | | | 65 | | |

| | | | | | | | | | | | | | | | | |
|---|---|---|---|---|---|---|---|---|---|---|---|---|---|---|---|---|
| tac | ggc | cgc | cat | gcg | gag | ctg | cgc | ttc | ttg | gac | ctg | gtt | cct | tct | ttg | 416 |
| Tyr | Gly | Arg | His | Ala | Glu | Leu | Arg | Phe | Leu | Asp | Leu | Val | Pro | Ser | Leu | |
| | | 70 | | | | | 75 | | | | | 80 | | | | |

| | | | | | | | | | | | | | | | | |
|---|---|---|---|---|---|---|---|---|---|---|---|---|---|---|---|---|
| cag | ttg | gac | ccg | gcc | cag | atc | tac | agg | gtc | act | tgg | ttc | atc | tcc | tgg | 464 |
| Gln | Leu | Asp | Pro | Ala | Gln | Ile | Tyr | Arg | Val | Thr | Trp | Phe | Ile | Ser | Trp | |
| | 85 | | | | | 90 | | | | | 95 | | | | | |

| | | | | | | | | | | | | | | | | |
|---|---|---|---|---|---|---|---|---|---|---|---|---|---|---|---|---|
| agc | ccc | tgc | ttc | tcc | tgg | ggc | tgt | gcc | ggg | gaa | gtg | cgt | gcg | ttc | ctt | 512 |
| Ser | Pro | Cys | Phe | Ser | Trp | Gly | Cys | Ala | Gly | Glu | Val | Arg | Ala | Phe | Leu | |
| 100 | | | | | 105 | | | | | 110 | | | | | | |

| | | | | | | | | | | | | | | | | |
|---|---|---|---|---|---|---|---|---|---|---|---|---|---|---|---|---|
| cag | gag | aac | aca | cac | gtg | aga | ctg | cgt | atc | ttc | gct | gcc | cgc | atc | tat | 560 |
| Gln | Glu | Asn | Thr | His | Val | Arg | Leu | Arg | Ile | Phe | Ala | Ala | Arg | Ile | Tyr | |
| 115 | | | | 120 | | | | | 125 | | | | | 130 | | |

| | | | | | | | | | | | | | | | | |
|---|---|---|---|---|---|---|---|---|---|---|---|---|---|---|---|---|
| gat | tac | gac | ccc | cta | tat | aag | gag | gca | ctg | caa | atg | ctg | cgg | gat | gct | 608 |
| Asp | Tyr | Asp | Pro | Leu | Tyr | Lys | Glu | Ala | Leu | Gln | Met | Leu | Arg | Asp | Ala | |
| | | | | 135 | | | | | 140 | | | | | 145 | | |

| | | | | | | | | | | | | | | | | |
|---|---|---|---|---|---|---|---|---|---|---|---|---|---|---|---|---|
| ggg | gcc | caa | gtc | tcc | atc | atg | acc | tac | gat | gaa | ttt | aag | cac | tgc | tgg | 656 |
| Gly | Ala | Gln | Val | Ser | Ile | Met | Thr | Tyr | Asp | Glu | Phe | Lys | His | Cys | Trp | |
| | | | 150 | | | | | 155 | | | | | 160 | | | |

| | | | | | | | | | | | | | | | | |
|---|---|---|---|---|---|---|---|---|---|---|---|---|---|---|---|---|
| gac | acc | ttt | gtg | gac | cac | cag | gga | tgt | ccc | ttc | cag | ccc | tgg | gat | gga | 704 |
| Asp | Thr | Phe | Val | Asp | His | Gln | Gly | Cys | Pro | Phe | Gln | Pro | Trp | Asp | Gly | |
| | | 165 | | | | | 170 | | | | | 175 | | | | |

| | | | | | | | | | | | | | | | | |
|---|---|---|---|---|---|---|---|---|---|---|---|---|---|---|---|---|
| cta | gat | gag | cac | agc | caa | gcc | ctg | agt | ggg | agg | ctg | cgg | gcc | att | ctc | 752 |
| Leu | Asp | Glu | His | Ser | Gln | Ala | Leu | Ser | Gly | Arg | Leu | Arg | Ala | Ile | Leu | |
| | 180 | | | | | 185 | | | | | 190 | | | | | |

| | | | | | | |
|---|---|---|---|---|---|---|
| cag | aat | cag | gga | aac | tga aggatgggcc tcagtctcta aggaaggcag | 800 |
| Gln | Asn | Gln | Gly | Asn | | |
| 195 | | | | | | |

| | |
|---|---|
| agacctgggt tgagcagcag aataaaagat cttcttccaa gaaatgcaaa cagaccgttc | 860 |
| accaccatct ccagctgctc acagacgcca gcaaagcagt atgctcccga tcaagtagat | 920 |
| ttttaaaaaa tcagagtggg ccgggcgcgg tggctcacgc ctgtaatccc agcactttgg | 980 |
| aggccaaggc gggtggatca cgaggtcagg agatcgagac catcctggct aacacggtga | 1040 |
| aaccctgtct ctactaaaaa tacaaaaaat tagccaggcg tggtggcggg cgcctgtagt | 1100 |
| cccagctact ctggaggctg aggcaggaga gtagcgtgaa cccgggaggc agagcttgcg | 1160 |
| gtgagccgag attgcgctac tgcactccag cctgggcgac agtaccagac tccatctcaa | 1220 |
| aaaaaaaaaa accagactga attaatttta actgaaaatt tctcttatgt tccaagtaca | 1280 |
| caatagtaag attatgctca atattctcag aataattttc aatgtattaa tgaaatgaaa | 1340 |
| tgataatttg gcttcatatc tagactaaca caaaattaag aatcttccat aattgctttt | 1400 |
| gctcagtaac tgtgtcatga attgcaagag tttccacaaa cact | 1444 |

<210> SEQ ID NO 2
<211> LENGTH: 199
<212> TYPE: PRT
<213> ORGANISM: Homo sapiens

<400> SEQUENCE: 2

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr

```
                    20                  25                  30

Leu Cys Tyr Glu Val Glu Arg Leu Asp Asn Gly Thr Ser Val Lys Met
         35                  40                  45

Asp Gln His Arg Gly Phe Leu His Asn Gln Ala Lys Asn Leu Leu Cys
     50                  55                  60

Gly Phe Tyr Gly Arg His Ala Glu Leu Arg Phe Leu Asp Leu Val Pro
 65                  70                  75                  80

Ser Leu Gln Leu Asp Pro Ala Gln Ile Tyr Arg Val Thr Trp Phe Ile
                 85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Tyr Asp Tyr Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195

<210> SEQ ID NO 3
<211> LENGTH: 1560
<212> TYPE: DNA
<213> ORGANISM: Homo sapiens
<220> FEATURE:
<221> NAME/KEY: CDS
<222> LOCATION: (56)..(1204)

<400> SEQUENCE: 3
cacagagctt caaaaaaaga gcgggacagg gacaagcgta tctaagaggc tgaac atg     58
                                                              Met
                                                                1 aat cca cag atc aga aat ccg atg gag cgg atg tat cga gac aca ttc    106
Asn Pro Gln Ile Arg Asn Pro Met Glu Arg Met Tyr Arg Asp Thr Phe
        5                  10                  15 tac gac aac ttt gaa aac gaa ccc atc ctc tat ggt cgg agc tac act    154
Tyr Asp Asn Phe Glu Asn Glu Pro Ile Leu Tyr Gly Arg Ser Tyr Thr
     20                  25                  30 tgg ctg tgc tat gaa gtg aaa ata aag agg ggc cgc tca aat ctc ctt    202
Trp Leu Cys Tyr Glu Val Lys Ile Lys Arg Gly Arg Ser Asn Leu Leu
 35                  40                  45 tgg gac aca ggg gtc ttt cga ggc cag gtg tat ttc aag cct cag tac    250
Trp Asp Thr Gly Val Phe Arg Gly Gln Val Tyr Phe Lys Pro Gln Tyr
 50                  55                  60                  65 cac gca gaa atg tgc ttc ctc tct tgg ttc tgt ggc aac cag ctg cct    298
His Ala Glu Met Cys Phe Leu Ser Trp Phe Cys Gly Asn Gln Leu Pro
                 70                  75                  80 gct tac aag tgt ttc cag atc acc tgg ttt gta tcc tgg acc ccc tgc    346
Ala Tyr Lys Cys Phe Gln Ile Thr Trp Phe Val Ser Trp Thr Pro Cys
             85                  90                  95 ccg gac tgt gtg gcg aag ctg gcc gaa ttc ctg tct gag cac ccc aat    394
Pro Asp Cys Val Ala Lys Leu Ala Glu Phe Leu Ser Glu His Pro Asn
        100                 105                 110 gtc acc ctg acc atc tct gcc gcc cgc ctc tac tac tac tgg gaa aga    442
```

```
      Val Thr Leu Thr Ile Ser Ala Ala Arg Leu Tyr Tyr Tyr Trp Glu Arg
          115                 120                 125 gat tac cga agg gcg ctc tgc agg ctg agt cag gca gga gcc cgc gtg     490
Asp Tyr Arg Arg Ala Leu Cys Arg Leu Ser Gln Ala Gly Ala Arg Val
130                 135                 140                 145 aag atc atg gac tat gaa gaa ttt gca tac tgc tgg gaa aac ttt gtg     538
Lys Ile Met Asp Tyr Glu Glu Phe Ala Tyr Cys Trp Glu Asn Phe Val
                    150                 155                 160 tac aat gaa ggt cag caa ttc atg cct tgg tac aaa ttc gat gaa aat     586
Tyr Asn Glu Gly Gln Gln Phe Met Pro Trp Tyr Lys Phe Asp Glu Asn
                165                 170                 175 tat gca ttc ctg cac cgc acg cta aag gag att ctc aga tac ctg atg     634
Tyr Ala Phe Leu His Arg Thr Leu Lys Glu Ile Leu Arg Tyr Leu Met
            180                 185                 190 gat cca gac aca ttc act ttc aac ttt aat aat gac cct ttg gtc ctt     682
Asp Pro Asp Thr Phe Thr Phe Asn Phe Asn Asn Asp Pro Leu Val Leu
        195                 200                 205 cga cgg cgc cag acc tac ttg tgc tat gag gtg gag cgc ctg gac aat     730
Arg Arg Arg Gln Thr Tyr Leu Cys Tyr Glu Val Glu Arg Leu Asp Asn
210                 215                 220                 225 ggc acc tgg gtc ctg atg gac cag cac atg ggc ttt cta tgc aac gag     778
Gly Thr Trp Val Leu Met Asp Gln His Met Gly Phe Leu Cys Asn Glu
                    230                 235                 240 gct aag aat ctt ctc tgt ggc ttt tac ggc cgc cat gcg gag ctg cgc     826
Ala Lys Asn Leu Leu Cys Gly Phe Tyr Gly Arg His Ala Glu Leu Arg
                245                 250                 255 ttc ttg gac ctg gtt cct tct ttg cag ttg gac ccg gcc cag atc tac     874
Phe Leu Asp Leu Val Pro Ser Leu Gln Leu Asp Pro Ala Gln Ile Tyr
            260                 265                 270 agg gtc act tgg ttc atc tcc tgg agc ccc tgc ttc tcc tgg ggc tgt     922
Arg Val Thr Trp Phe Ile Ser Trp Ser Pro Cys Phe Ser Trp Gly Cys
        275                 280                 285 gcc ggg gaa gtg cgt gcg ttc ctt cag gag aac aca cac gtg aga ctg     970
Ala Gly Glu Val Arg Ala Phe Leu Gln Glu Asn Thr His Val Arg Leu
290                 295                 300                 305 cgc atc ttc gct gcc cgc atc tat gat tac gac ccc cta tat aag gag    1018
Arg Ile Phe Ala Ala Arg Ile Tyr Asp Tyr Asp Pro Leu Tyr Lys Glu
                    310                 315                 320 gcg ctg caa atg ctg cgg gat gct ggg gcc caa gtc tcc atc atg acc    1066
Ala Leu Gln Met Leu Arg Asp Ala Gly Ala Gln Val Ser Ile Met Thr
                325                 330                 335 tac gat gag ttt gag tac tgc tgg gac acc ttt gtg tac cgc cag gga    1114
Tyr Asp Glu Phe Glu Tyr Cys Trp Asp Thr Phe Val Tyr Arg Gln Gly
            340                 345                 350 tgt ccc ttc cag ccc tgg gat gga cta gag gag cac agc caa gcc ctg    1162
Cys Pro Phe Gln Pro Trp Asp Gly Leu Glu Glu His Ser Gln Ala Leu
        355                 360                 365 agt ggg agg ctg cgg gcc att ctc cag aat cag gga aac tga             1204
Ser Gly Arg Leu Arg Ala Ile Leu Gln Asn Gln Gly Asn
370                 375                 380 aggatgggcc tcagtctcta aggaaggcag agacctgggt tgagcagcag aataaaagat  1264
cttcttccaa gaaatgcaaa cagaccgttc accaccatct ccagctgctc acagacacca  1324
gcaaagcaat gtgctcctga tcaagtagat tttttaaaaa tcagagtcaa ttaattttaa  1384
ttgaaaattt ctcttatgtt ccaagtgtac aagagtaaga ttatgctcaa tattcccaga  1444
atagttttca atgtattaat gaagtgatta attggctcca tatttagact aataaaacat  1504
taagaatctt ccataattgt ttccacaaac actaaaaaaa aaaaaaaaaa aaaaaa      1560
```

<210> SEQ ID NO 4
<211> LENGTH: 382
<212> TYPE: PRT
<213> ORGANISM: Homo sapiens

<400> SEQUENCE: 4

Met Asn Pro Gln Ile Arg Asn Pro Met Glu Arg Met Tyr Arg Asp Thr
1               5                   10                  15

Phe Tyr Asp Asn Phe Glu Asn Glu Pro Ile Leu Tyr Gly Arg Ser Tyr
            20                  25                  30

Thr Trp Leu Cys Tyr Glu Val Lys Ile Lys Arg Gly Arg Ser Asn Leu
        35                  40                  45

Leu Trp Asp Thr Gly Val Phe Arg Gly Gln Val Tyr Phe Lys Pro Gln
    50                  55                  60

Tyr His Ala Glu Met Cys Phe Leu Ser Trp Phe Cys Gly Asn Gln Leu
65                  70                  75                  80

Pro Ala Tyr Lys Cys Phe Gln Ile Thr Trp Phe Val Ser Trp Thr Pro
                85                  90                  95

Cys Pro Asp Cys Val Ala Lys Leu Ala Glu Phe Leu Ser Glu His Pro
            100                 105                 110

Asn Val Thr Leu Thr Ile Ser Ala Ala Arg Leu Tyr Tyr Tyr Trp Glu
        115                 120                 125

Arg Asp Tyr Arg Arg Ala Leu Cys Arg Leu Ser Gln Ala Gly Ala Arg
    130                 135                 140

Val Lys Ile Met Asp Tyr Glu Glu Phe Ala Tyr Cys Trp Glu Asn Phe
145                 150                 155                 160

Val Tyr Asn Glu Gly Gln Gln Phe Met Pro Trp Tyr Lys Phe Asp Glu
                165                 170                 175

Asn Tyr Ala Phe Leu His Arg Thr Leu Lys Glu Ile Leu Arg Tyr Leu
            180                 185                 190

Met Asp Pro Asp Thr Phe Thr Phe Asn Phe Asn Asn Asp Pro Leu Val
        195                 200                 205

Leu Arg Arg Arg Gln Thr Tyr Leu Cys Tyr Glu Val Glu Arg Leu Asp
    210                 215                 220

Asn Gly Thr Trp Val Leu Met Asp Gln His Met Gly Phe Leu Cys Asn
225                 230                 235                 240

Glu Ala Lys Asn Leu Leu Cys Gly Phe Tyr Gly Arg His Ala Glu Leu
                245                 250                 255

Arg Phe Leu Asp Leu Val Pro Ser Leu Gln Leu Asp Pro Ala Gln Ile
            260                 265                 270

Tyr Arg Val Thr Trp Phe Ile Ser Trp Ser Pro Cys Phe Ser Trp Gly
        275                 280                 285

Cys Ala Gly Glu Val Arg Ala Phe Leu Gln Glu Asn Thr His Val Arg
    290                 295                 300

Leu Arg Ile Phe Ala Ala Arg Ile Tyr Asp Tyr Asp Pro Leu Tyr Lys
305                 310                 315                 320

Glu Ala Leu Gln Met Leu Arg Asp Ala Gly Ala Gln Val Ser Ile Met
                325                 330                 335

Thr Tyr Asp Glu Phe Glu Tyr Cys Trp Asp Thr Phe Val Tyr Arg Gln
            340                 345                 350

Gly Cys Pro Phe Gln Pro Trp Asp Gly Leu Glu Glu His Ser Gln Ala
        355                 360                 365

Leu Ser Gly Arg Leu Arg Ala Ile Leu Gln Asn Gln Gly Asn
    370                 375                 380